United States Patent [19]
Breslow et al.

[11] Patent Number: 5,668,179
[45] Date of Patent: Sep. 16, 1997

[54] POTENT INDUCERS OF TERMINAL DIFFERENTIATION AND METHOD OF USE THEREOF

[75] Inventors: Ronald Breslow, Englewood, N.J.; Paul A. Marks, Bridgewater, Conn.; Richard A. Rifkind, New York, N.Y.

[73] Assignees: The Trustees of Columbia University in the City of New York; Sloan-Kettering Institute for Cancer Research, both of New York, N.Y.

[21] Appl. No.: 485,619

[22] Filed: Jun. 7, 1995

Related U.S. Application Data

[62] Division of Ser. No. 164,639, Dec. 9, 1993, abandoned, which is a continuation of Ser. No. 701,323, May 6, 1991, abandoned, which is a continuation of Ser. No. 270,963, Nov. 14, 1988, abandoned.

[51] Int. Cl.$^6$ .................................................. A61K 31/16
[52] U.S. Cl. .................................................. 514/629
[58] Field of Search .................................. 564/153, 159; 514/629

[56] References Cited

U.S. PATENT DOCUMENTS 4,801,748  1/1989  Murahashi ........................... 564/126

OTHER PUBLICATIONS

Morrison, R.T. and Boyd, R. N., Organic Chemistry (3rd ed. Allyn and Bacon) (Boston) (1973) p. 755.
Reuben, R. C., et al., Inducers of Erythroleukemic Differentiation. J. Biol. Chem. (1978) 253 (12): 4214–4218.
Tanaka, M., et al., Induction of Erythroid Differentiation in Murine Virus Infected Erythroleukemia Cells by Highly Polar Compounds. Proc. Natl. Acad. Sci. USA (1975) 72(3): 1003–1006.
Reuben,Roberta C., et al., A New Group of Potent Inducers Of Differentiation in Murine Erythroleukemia Cells. Proc. Natl. Acad. Sci. USA (1976) 73(3): 862–866.

Primary Examiner—José G. Dees
Assistant Examiner—B. Bembenick
Attorney, Agent, or Firm—John P. White

[57] ABSTRACT

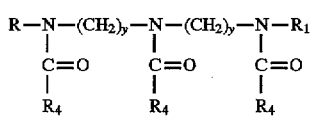

wherein each of R, $R_1$, and $R_4$ is a hydrogen atom or a methyl, ethyl or propyl group, R and $R_1$ are the same and R and $R_4$ are the same or different; and wherein y is 4, 5, 6 or 7.

The invention also concerns a method of selectively inducing terminal differentiation of neoplastic cells and thereby inhibiting proliferation of such cells which comprises contacting the cells under suitable condition with an amount of the compound effect to selectively induce terminal differentiation.

Moreover, the invention provides a method of treating a patient having a tumor characterized by proliferation of neoplastic cells which comprises administering to the patient an amount of the compound effective to selectively induce terminal differentiation of such neoplastic cells, thereby inhibiting their proliferation and suppressing oncogenicity.

Lastly, the present invention provides a pharmaceutical composition comprising a pharmaceutically acceptable carrier and the compound in an amount effective less than an amount which would cause toxicity in the patient.

10 Claims, 7 Drawing Sheets

FIG. 1A

| K-135 conc. | cell count | B+ cells |
|---|---|---|
| 1mM | $2.4 \times 10^6$ | 68-69 |
| 2mM | $1.9 \times 10^6$ | 77-80 |
| 3mM | $1.2 \times 10^6$ | 78-81 |
| 4mM | $0.5 \times 10^6$ | 3-4 |
| 5mM | $0.2 \times 10^6$ | 0-1 |

Control cell ⟶ 0-1

5mM HMBA ⟶ 89-88

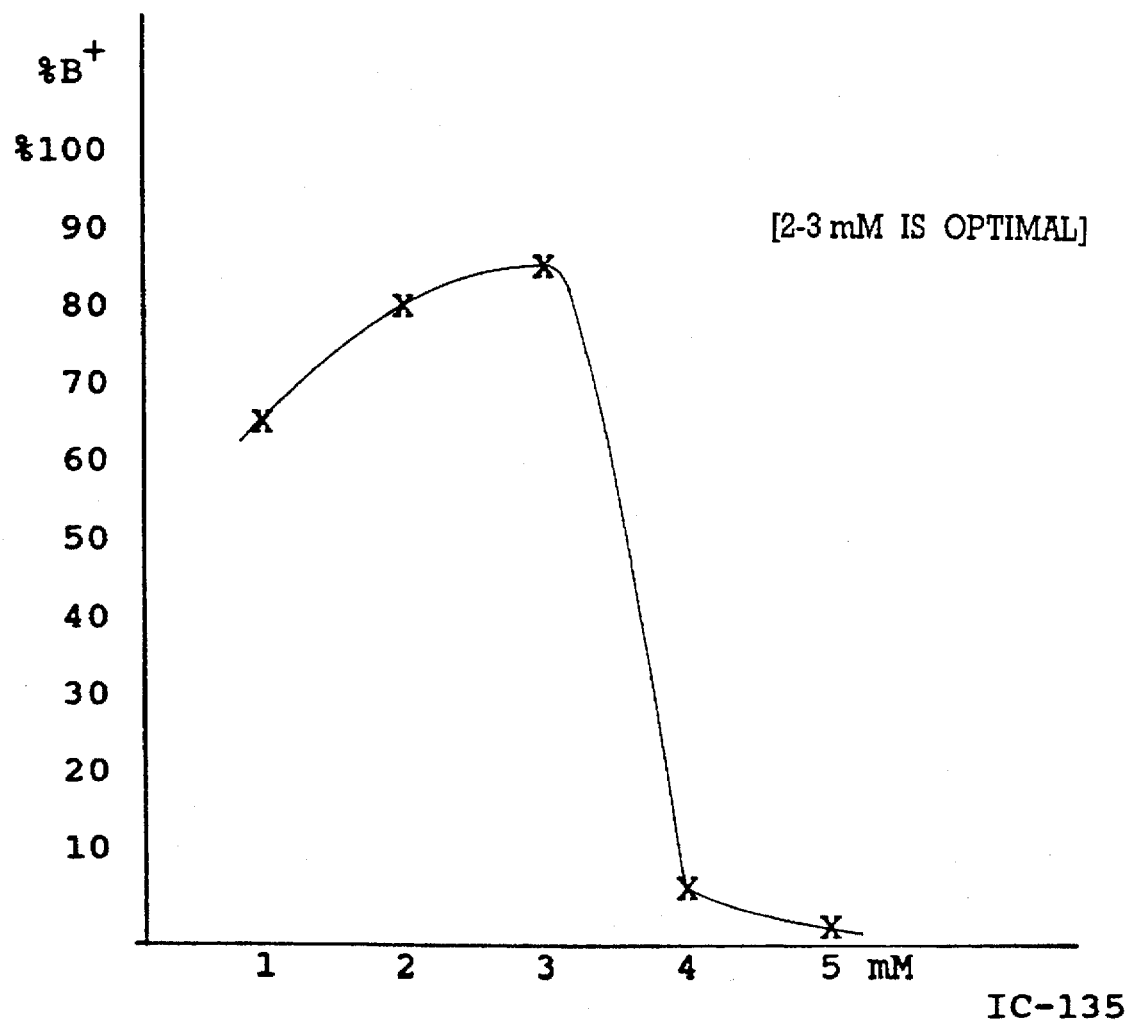

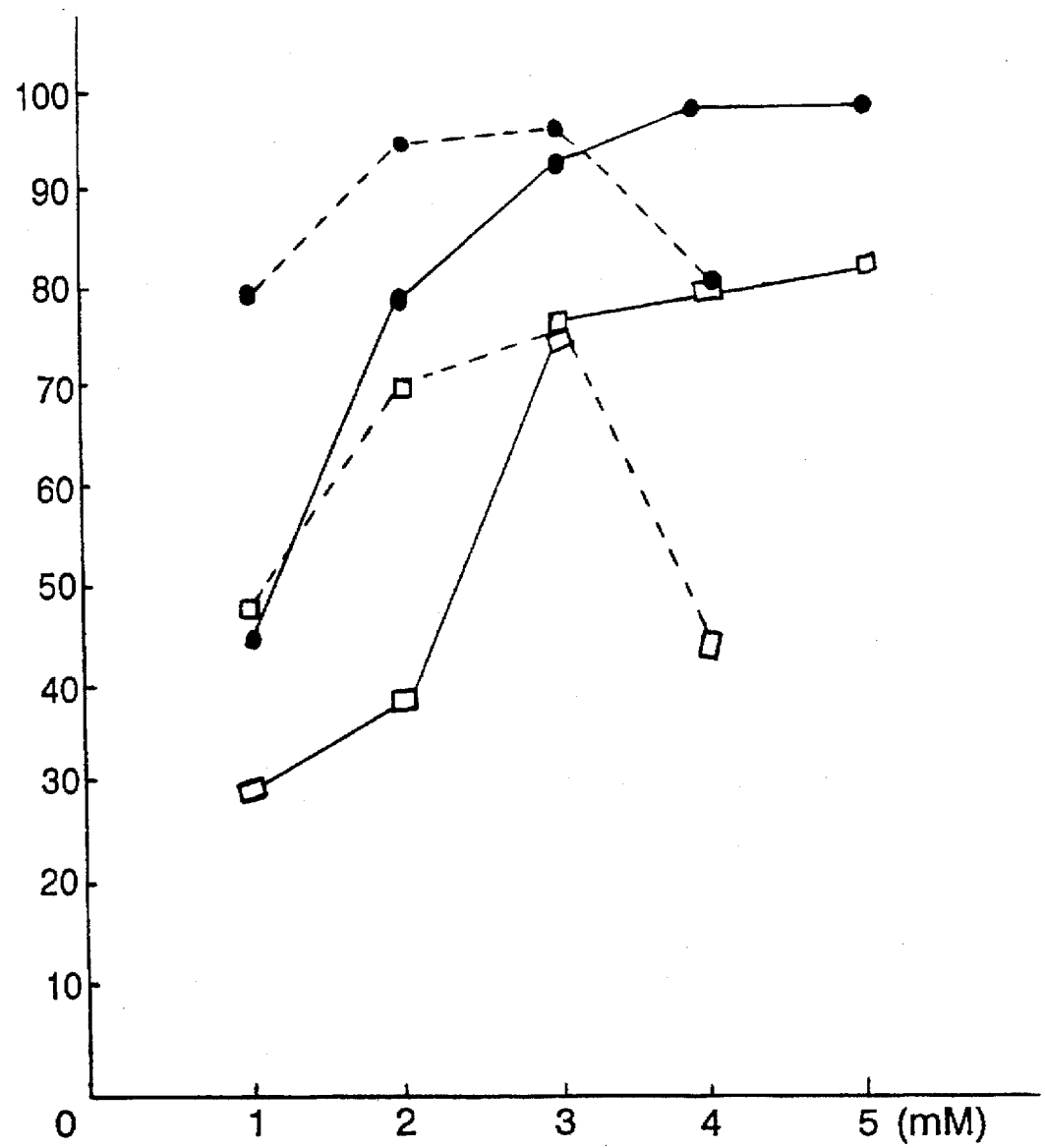

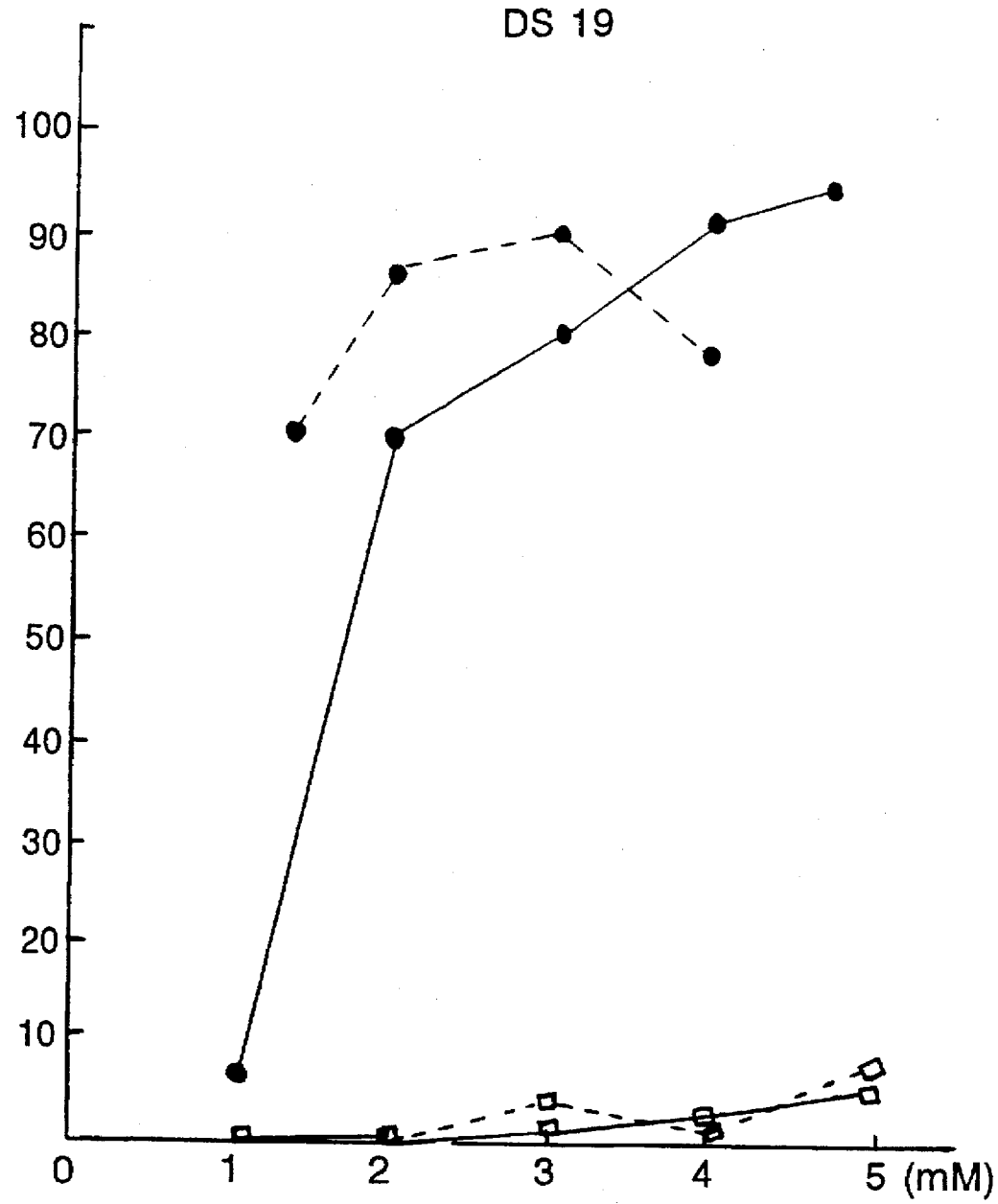

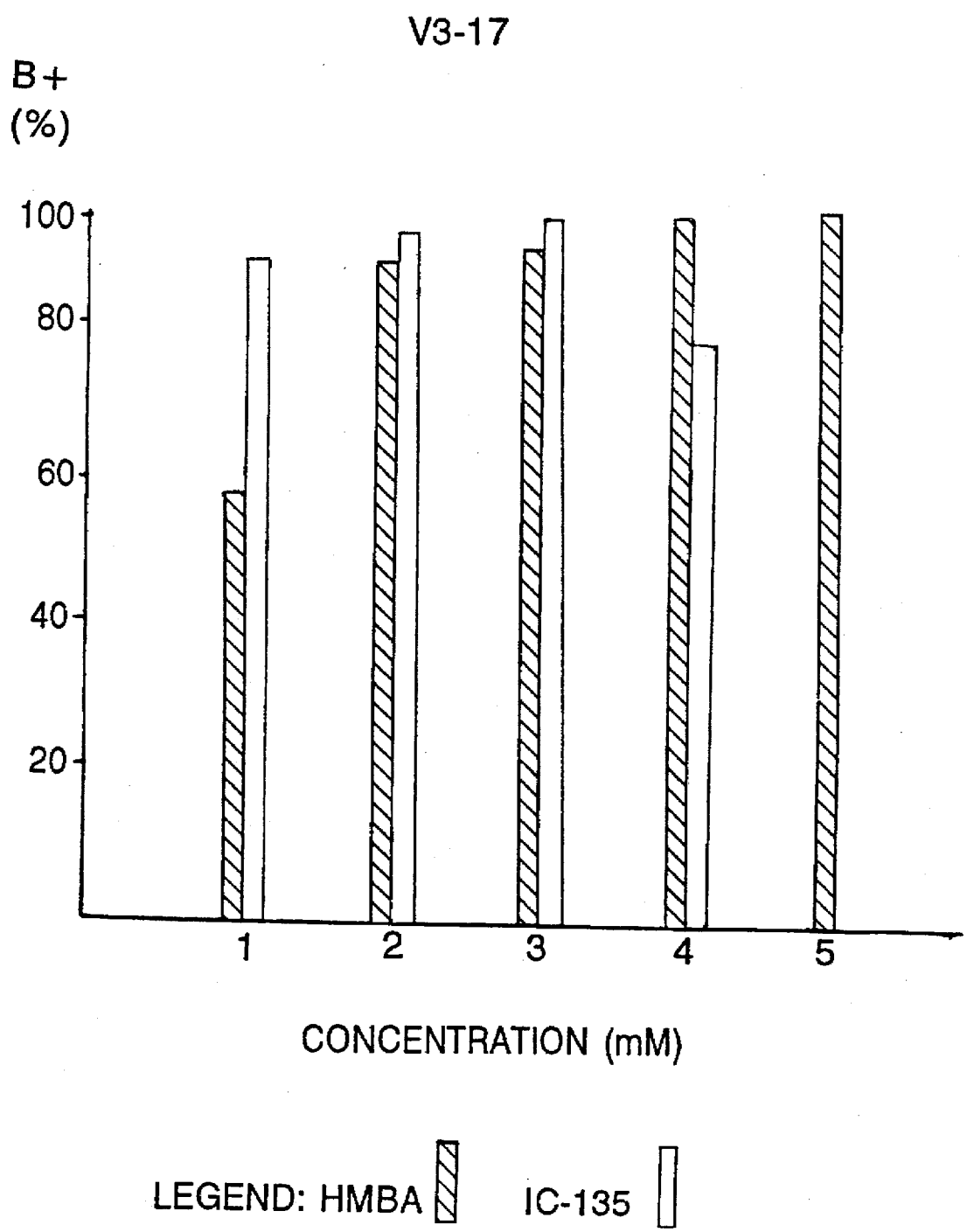

POTENT INDUCERS OF TERMINAL DIFFERENTIATION AND METHOD OF USE THEREOF

This is a divisional of U.S. Ser. No. 08/164,639, filed Dec. 9, 1993 (now abandoned), which is a continuation of U.S. Ser. No. 07/701,323, filed May 6, 1991, now abandoned, which is a continuation of U.S. Ser. No. 07/270,963, filed Nov. 14, 1988, now abandoned.

BACKGROUND OF THE INVENTION

Throughout this application various publications are referenced by arabic numerals within parentheses. Full citations for these publications may be found at the end of the specification immediately preceding the claims. The disclosures of these publications in their entireties are hereby incorporated by reference into this application in order to more fully describe the state of the art to which this invention pertains.

Cancer is a disorder in which a population of cells has become, in varying degrees, unresponsive to the control mechanisms which normally govern proliferation and differentiation. For many years there have been two principal strategies for chemotherapeutic treatment of cancer: a) blocking hormone-dependent tumor cell proliferation by interference with the production or peripheral action of sex hormones; and b) killing cancer cells directly by exposing them to cytotoxic substances, which injure both neoplastic and normal cell populations. Relatively recently, cancer therapy is also being attempted by the induction of terminal differentiation of the neoplastic cells (10). In cell culture models differentiation has been reported by exposure of cells to a variety of stimuli, including: cyclic AMP and retinoic acid (1,2), aclarubicin and other anthracyclines (3), and polar planar compounds, of which the most extensively studied is hexamethylene bisacetamide (HMBA) (4–5, 9).

HMBA is capable of inducing phenotypic changes consistent with differentiation in a broad variety of cell lines (6). The characteristics of the drug-induced effect have been most extensively studied in the Friend murine erythroleukemia cell system (MELC) (6–9). MELC induction of differentiation is both time and concentration dependent. The minimum concentration required to demonstrate an effect in vitro in most strains is 2 to 3 mM; the minimum duration of continuous exposure generally required to induce differentiation in a substantial portion (>20%) of the population without continuing drug exposure is about 36 hours.

The present invention provides new chemical inducers which are 2–5 times more active then HMBA. It has unexpectedly been found that compounds having two or more nonpolar components connected by a polar group and having polar groups on the termini of the compound are effective inducers of terminal differentiation. For instance, bis-hexamethylene triacetamide, which comprises three acetamide groups connected by two six-carbon chains, has been found to be a potent inducer of terminal differentiation in MELC.

This new class of compounds of the present invention may be useful for selectively inducing terminal differentiation of neoplastic cells and therefore aid in treatment of tumors in patients.

SUMMARY OF THE INVENTION

The invention provides a class of compounds having the structure:

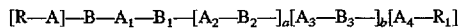

wherein each of A, $A_1$, $A_2$, $A_3$, and $A_4$ represent a polar group which comprises a nitrogen, sulfur or oxygen atom and wherein each of A, $A_1$, $A_2$, $A_3$, and $A_4$ may independently be the same as, or different from, the others of A, $A_1$, $A_2$, $A_3$, and A4;

wherein each of R and $R_1$ is a hydrogen atom; a lower alkyl, alkenyl, or alkynyl group; or a group having the structure:

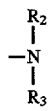

each of $R_2$ and $R_3$ being a hydrogen atom or a lower alkyl, alkenyl, or alkynyl group; and wherein each of R, $R_1$, $R_2$ and $R_3$ may independently be the same as, or different from, the others of R, $R_1$, $R_2$ and $R_3$;

wherein each of [R—A] and [$A_4$—$R_1$] have a dipolar moment greater than about 2.7 Debye units;

wherein each of B, $B_1$, $B_2$, and $B_3$ represents a nonpolar group which comprises at least 4 atoms in a chain, the termini of which chains are attached to A and $A_1$, $A_1$ and $A_2$, $A_2$ and $A_3$, and $A_3$ and $A_4$, respectively; wherein each such atom is oxygen, nitrogen, carbon, or sulfur and wherein each of B, $B_1$, $B_2$, and $B_3$ may independently be the same as, or different from, the others of B, $B_1$, $B_2$, and $B_3$;

and wherein each of a and b is independently 0 or 1.

The invention also concerns a method of selectively inducing terminal differentiation of neoplastic cells and thereby inhibiting proliferation of such cells which comprises contacting the cells under suitable condition with an amount of the compound effective to selectively induce terminal differentiation.

Moreover, the invention provides a method of treating a patient having a tumor characterized by proliferation of neoplastic cells which comprises administering to the patient an amount of the compound effective to selectively induce terminal differentiation of such neoplastic cells, thereby inhibiting their proliferation, and suppressing oncogenicity.

Lastly, the present invention provides a pharmaceutical composition comprising a pharmaceutically acceptable carrier and the compound in an amount less than an amount which would cause toxicity in the patient.

BRIEF DESCRIPTION OF THE FIGURES

FIGS. 1A and 1B: Optimal concentration of IC-135 for inducement of terminal differentiation.

FIGS. 3A and 3B: Comparison of % cell committed for HMBA and IC-135 on V3.17 and DS19 cell lines.

FIGS. 4A and 4B: Comparison of B+% for HMBA and IC-135 on V3.17 and DS19 cell lines.

DETAILED DESCRIPTION OF THE INVENTION

Figure 2:
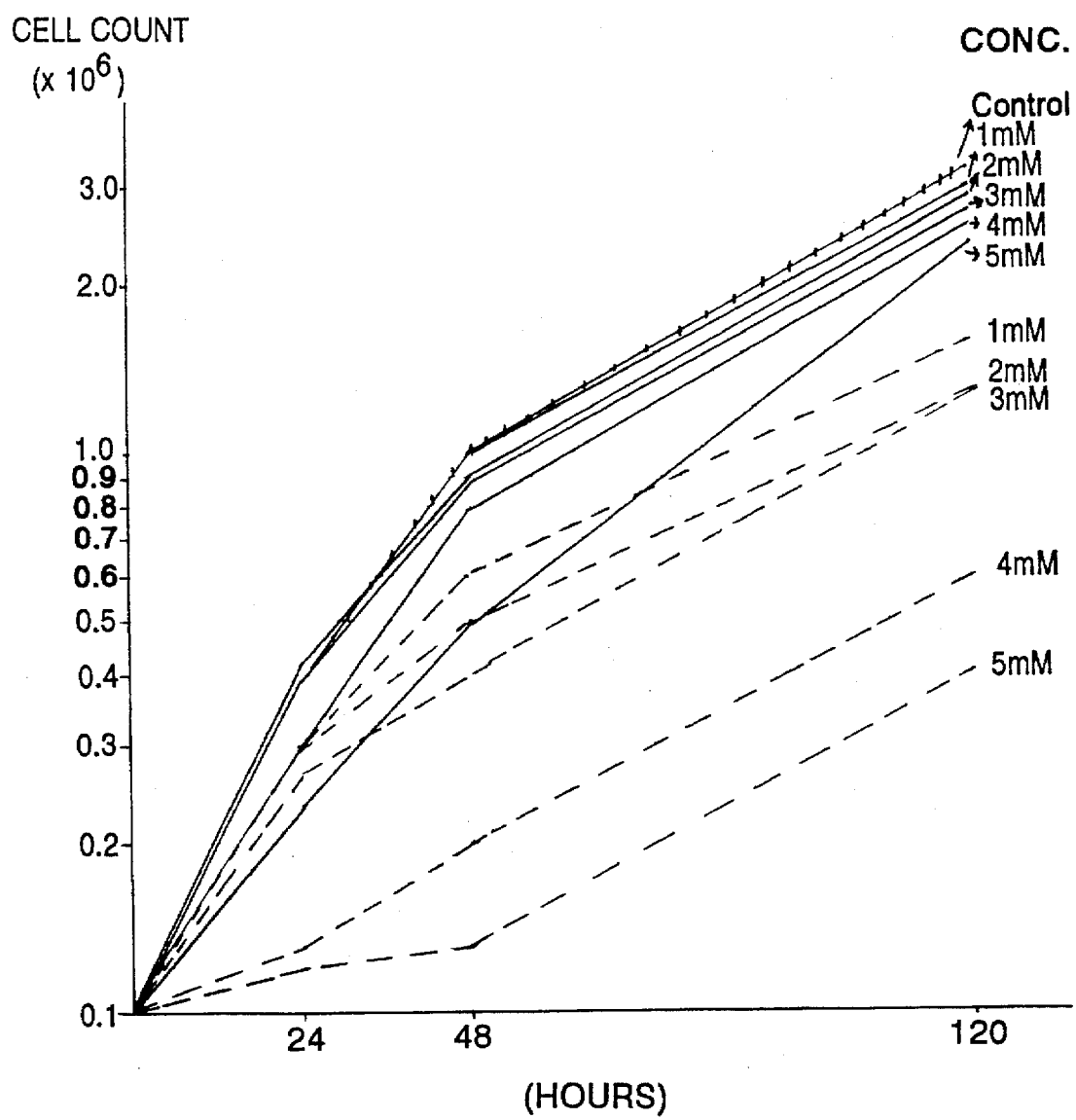
FIG. 2: Comparison of HMBA and IC-135 on DS19 cells.
Figure 4B:
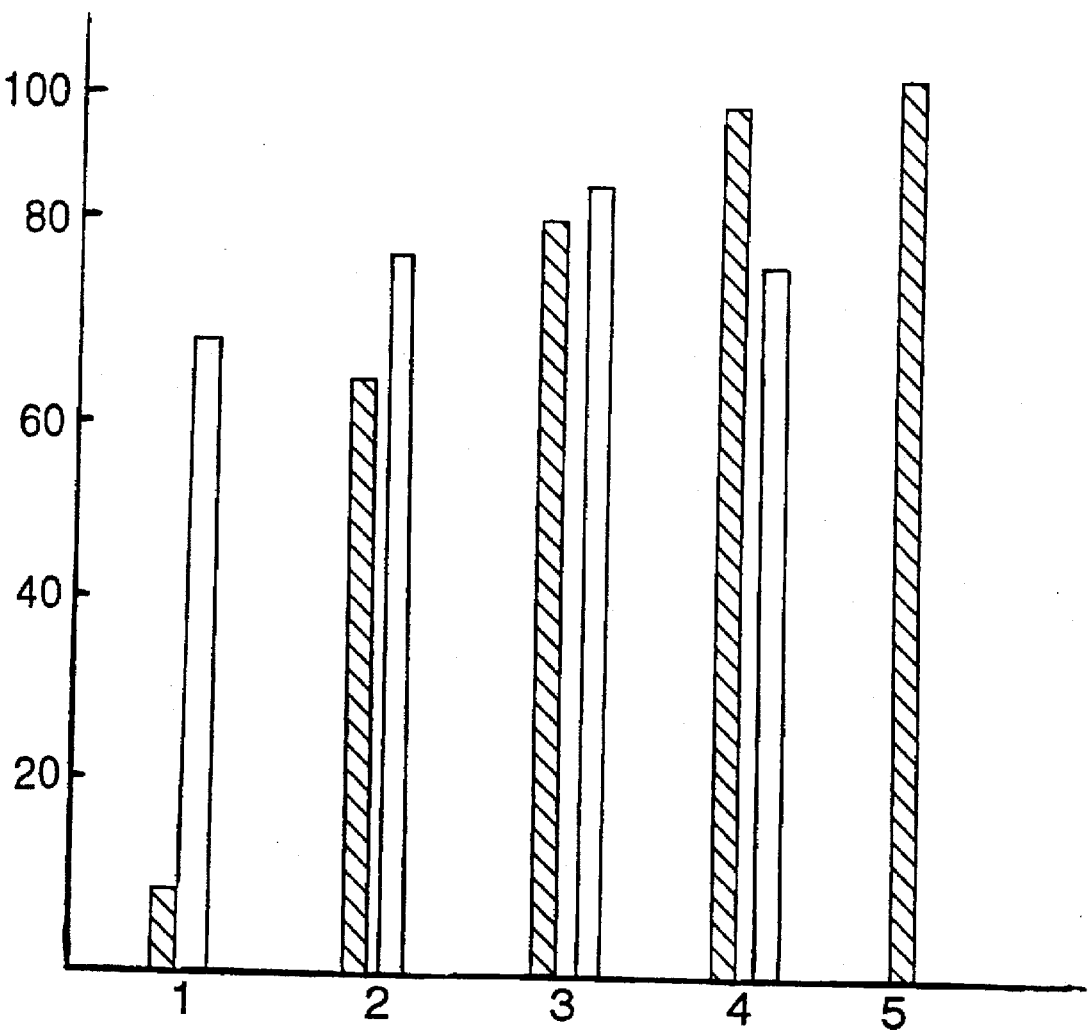

The invention provides a class of compounds having the structure:

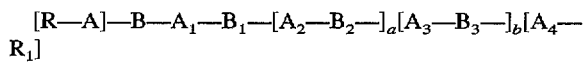

wherein each of A, A$_1$, A$_2$, A$_3$, and A$_4$ represent a polar group which comprises a nitrogen, sulfur or oxygen atom and wherein each of A, A$_1$, A$_2$, A$_3$, and A$_4$ may independently be the same as, or different from, the others of A, A$_1$, A$_2$, A$_3$, and A$_4$;

wherein each of R and R$_1$ is a hydrogen atom; a lower alkyl, alkenyl, or alkynyl group; or a group having the structure:

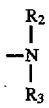

each of R$_2$ and R$_3$ being a hydrogen atom or a lower alkyl, alkenyl, or alkynyl group; and wherein each of R, R$_1$, R$_2$ and R$_3$ may independently be the same as, or different from, the others of R, R$_1$, R$_2$ and R$_3$;

wherein each of [R—A] and [A$_4$—R$_1$] have a dipolar moment greater than about 2.7 Debye units;

wherein each of B, B$_1$, B$_2$, and B$_3$ represents a nonpolar group which comprises at least 4 atoms in a chain, the termini of which chains are attached to A and A$_1$, A$_1$ and A$_2$, A$_2$ and A$_3$, and A$_3$ and A$_4$, respectively; wherein each such atom is oxygen, nitrogen, carbon, or sulfur and wherein each of B, B$_1$, B$_2$, and B$_3$ may independently be the same as, or different from, the others of B, B$_1$, B$_2$, and B$_3$;

and wherein each of a and b is independently 0 or 1.

The compounds of the present invention are made up of two components. One component comprises a polar group, i.e. functional groups with significant dipole moments, such as amides, sulfoxides, amine oxides and related functional groups.

The terminal portions of the compound, represented by R—A and A$_4$—R$_1$, each have dipole moments greater than about 2.7 debye units. The polar groups within the compound, represented by —A$_1$, —A$_2$— and —A$_3$—, have significant dipolar moments but not necessarily in excess of 2.7 debye units. In the preferred embodiments, the polar groups are carbonyl radicals or bivalent radicals of an amide, a sulfoxide or a amine oxide. Each polar group need not necessarily be the same as the other polar groups. In the most preferred embodiments, the polar groups within the compound are the same as each other and the terminal polar groups are the same. Preferably, all the polar groups are amide groups attached to the compound at the nitrogen atom or at the carbon atom of the carbonyl radical. The amide group may comprise one or more hydrocarbon substituents, such as a lower alkyl or alkenyl groups, including branched or unbranched groups. The term "lower alkyl or alkenyl group" is intended to include saturated and unsaturated hydrocarbon groups with 1 to about 5 carbon atoms.

The embodiments where a and b are 0 and A is a carbonyl radical or a group having the structure:

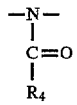

wherein R$_4$ is a hydrogen atom or a lower alkyl or alkenyl group, have proven to be the most useful embodiments to date.

Particularly preferred are compounds where a and b are 0, A is a carbonyl radical and R has the structure:

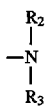

wherein R$_2$ and R$_3$ each is hydrogen atom, a methyl group or a ethyl group.

The compound also requires at least two nonpolar sections, designated B and B$_1$, which are attached to and connect polar groups. Additional nonpolar sections may also be present, e.g. B$_2$ when a is 1 and B$_3$ when b is 1. The nonpolar sections may comprise linear saturated hydrocarbon chains, linear unsaturated hydrocarbon chains containing one or more double or triple bonds, or saturated or unsaturated hydrocarbon chains containing one or more lower alkyl or alkenyl groups or small carbocyclic rings as substituents. In one of the preferred embodiments, the nonpolar groups are hydrocarbon chains comprising 4 to 7 methylene groups, especially preferred are hydrocarbon chains containing 6 carbon atoms.

The most preferred compounds for the practice of the present invention are those having the structures:

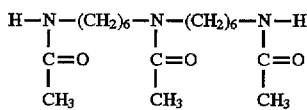

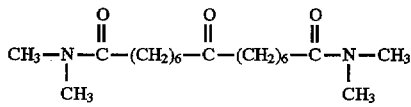

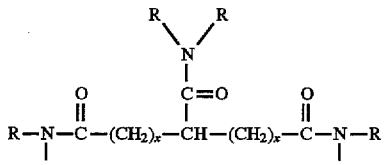

or

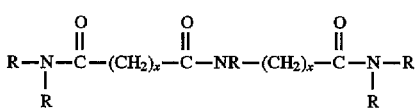

wherein R is hydrogen or a methyl group and x is 5 or 6.

The invention also concerns a method of selectively inducing terminal differentiation of neoplastic cells and thereby inhibiting proliferation of such cells which comprises contacting the cells under suitable condition with an amount of the compound effective to selectively induce terminal differentiation in the cells.

The contacting must be performed continuously for a prolonged period of time, i.e. for at least 48 hours, preferably for about 4–5 days or longer.

The method may be practiced in vivo or in vitro. If the method is practiced in vitro, contacting may be effective by incubating the cells with the compound. The concentration of the compound in contact with the cells should be from about 0.5 to 25 mM, preferably from about 1 mM to about 5 mM.

The invention also concerns a method of treating a patient having a tumor characterized by proliferation of neoplastic cells which comprises administering to the patient an amount of the compound effective to selectively induce terminal differentiation of such neoplastic cells thereby inhibiting their proliferation, and suppressing oncogenicity.

The method of the present invention is intended for the treatment of human patients with tumors. However, it is also likely that the method would be effective in the treatment of tumors in other animals. The term tumor is intended to include any cancer caused by the proliferation of neoplastic cells, such as lung cancer, acute lymphoid myeloma, bladder melanoma, renal carinoma, breast carcinoma, or colorectal carcinoma. The administration of the compound to the patient may be effected orally or parenterally. To date, administration intravenously has proven to be effective. The administration of the compound must be preformed continuously for a prolonged period of time, such as for at least 3 days preferably more than 5 days. In the most preferred embodiments, the administration is effected continuously for at least 10 days and is repeated at intervals wherein at each interval the administration is continuously effected for at least 10 days. For example, the administration may be effected at intervals as short as 5–10 days, up to about 25–35 days and continuously for at least 10 days during each such interval.

The amount of the compound administered to the patient is less than an amount which would cause toxicity in the patient. In the preferred embodiments, wherein the compound has the structure:

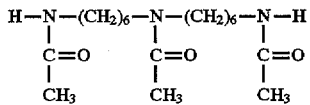

the amount of the compound which is administered to the patient is less than the amount which causes a concentration of the compound in the patient's plasma to equal or exceed the toxic level of the compound, i.e. about 1.5 mM. Preferably, the concentration of the compound in the patient's plasma is maintained at about 1.0 mM. It has been found that administration of the compound in an amount from about 5 gm/m$^2$/day to about 30 gm/m$^2$/day, particularly about 20 gm/m$^2$/day, is effective for the practice of the invention without producing toxicity in the patient. The optimal amount of the compound which should be administered to the patient in the practice of the present invention will depend on the particular compound used and the type of cancer being treated.

The invention also concerns a pharmaceutical composition comprising a pharmaceutically acceptable carrier, such as sterile pyrogen-free water, and the compound in an amount less than an amount which if administered intravenously or orally to a patient would cause the patient's blood plasma concentration of the compound to exceed toxic levels.

The invention is illustrated in the Experimental Detail section which follows. This section is set forth to aid in an understanding of the invention but is not intended to, and should not be construed to, limit in any way the invention as set forth in the claims which follow thereafter.

EXPERIMENTAL DETAILS

Manufacture of bis-Hexamethylenetriacetamide

A solution of 19.8 gm commercial bis-hexamethylenetriamine in 500 ml of 1,4-dioxane was made up at room temperature under argon. Then 44.8 ml. of triethylamine was added, and 20.3 ml. of acetyl chloride was slowly added with stirring. After two hours of stirring at room temperature the triethylamine hydrochloride was removed by filtration and the filtrate was concentrated in vacuo. The product triacetyl compound was isolated as a clear viscous oil at about 90% yield by chromatography on basic alumina using isopropanol/ethyl acetate/dichloromethane in the ratio 2/3/5. On thin layer plates of basic alumina with this solvent mixture the product had an $R_f$ of ca. 0.6.

The mass spectrum (chemical ionization, $NH_3$ carrier) showed peaks at 342 (100%, M+1), 227 (10%) and 115 (22%). The infrared spectrum (thin film on NaCl) had bands at 3288, 2931, 2858, 1627, 1560, 1437, 1373, and 1292 cm$^{-1}$. In the proton NMR (CDCl$_3$) the acetyl groups appeared at δ2.06 (3 H) and 1.96 (6 H) as singlets, the two NH protons appeared at δ6.10 as a broad signal, while the methylene protons appeared as multiplets with the expected intensities in the regions of δ3.12 to 3.30 and 1.21 to 1.54.

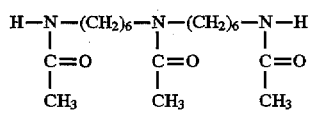

bis-Hexamethylenetriacetamide (IC-135)

Induced Terminal Differentiation in Cell Cultures

Cell cultures were grown in the presence of different concentrations of Hexamethylenebisacetamide (HMBA)

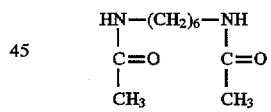

and bis-Hexamethylenetriacetamide (IC-135).

At 1, 2 and 5 days, the cell densities and the percentage of cells that were benzidine reactive (B+) were measured. Table 1 shows the cell densities, B+%, and percent of cells commited for cell lines DS19 and V3.17 grown in 1 mM to 5 mM of HMBA and IC-135. FIGS. 1A and 1B, 2, 3A and B, and 4A and B are graphical representations of the data presented in Table 1.

Table 2 shows cell counts for days 1, 2 and 5 and percentage of cells committed and benzidine reactive (B+) at day 5 for cell lines DS-19, V3.17 and DR-10 grown in 5 mM of HMBA and 0.5 to 3 mM of IC-135.

As can be seen in the Tables and Figures, IC-135 is more reactive in the tested cell lines at lower concentrations than HMBA.

TABLE 1

| | | | 24 h | | 48 h | | 120 h | | commitment | |
|---|---|---|---|---|---|---|---|---|---|---|
| | | | cell count | B+ | cell count | B+ | cell count | B+ | 24 h | 48 h |
| HMBA | 1 mM | DS19 | 0.4 | 0-1 | 1.0 | 0-1 | $3.0 \times 10^6$ | 8% | 0-1 | 6-8 |
| | | $V_317$ | 0.38 | 8-9 | 0.8 | 33% | 2.8 | 58% | 30% | 43% |
| | 2 mM | DS19 | 0.42 | 0-1 | 0.9 | 0-1 | 2.9 | 64% | 0-1 | 71% |
| | | $V_317$ | 0.4 | 7-9 | 0.8 | 72% | 2.6 | 89% | 39% | 79% |
| | 3 mM | DS19 | 0.4 | 0-1 | 0.9 | 2 | 2.8 | 82% | 0-1 | 81% |
| | | $V_317$ | 0.3 | 9-10 | 0.4 | 80% | 1.8 | 91% | 77% | 94% |
| | 4 mM | DS19 | 0.3 | 0-1 | 0.8 | 11% | 2.6 | 94% | 4% | 92% |
| | | $V_317$ | 0.28 | 9-13 | 0.4 | 88% | 1.6 | 96% | 80% | 99% |
| | 5 mM | DS19 | 0.23 | 0-1 | 0.5 | 14% | 2.4 | 98% | 6% | 96% |
| | | $V_317$ | 0.22 | 9-14 | 0.5 | 89% | 1.6 | 99% | 83% | 98% |
| IC-135 | 1 mM | DS19 | 0.3 | 0-1 | 0.6 | 0-1 | 1.6 | 69% | 0-1 | 71% |
| | | $V_317$ | 0.3 | 8-9 | 0.6 | 83% | 1.3 | 89% | 58% | 89% |
| | 2 mM | DS19 | 0.3 | 0-1 | 0.5 | 0-1 | 1.3 | 79% | 1-2 | 87% |
| | | $V_317$ | 0.29 | 7-6 | 0.4 | 88% | 1.3 | 94% | 70% | 95% |
| | 3 mM | DS19 | 0.27 | 0-1 | 0.4 | 0-1 | 1.3 | 86% | 5-4 | 91% |
| | | $V_317$ | 0.12 | 8-6 | 0.3 | 89% | 0.9 | 96% | 76% | 97% |
| | 4 mM | DS19 | 0.13 | 0-1 | 0.2 | 0-1 | 0.6 | 78% | 2-1 | 79% |
| | | $V_317$ | 0.18 | 6-8 | 0.19 | 34% | 0.5 | 79% | 44% | 81% |
| | 5 mM | DS19 | 0.12 | 0 | 0.13 | 0-1 | 0.4 | — | 8% | — |
| | | $V_317$ | 0.12 | 8-11 | 0.12 | 0-1 | 0.3 | — | 0-1 | — |
| CONTROL | | | 0.4 | 5-9 | 1.0 | 0-1 | $3.1 \times 10^6$ | 0-1 | 0-1 | 0-1 |

IC-135 50 mM Stock.   40 λ - 1 mM
                     200 λ - 5 mM
HMBA 200 mM Stock  10 λ - 1 mM
                   50 λ - 5 mM.

TABLE 2

TESTING OF IC-135 ON DIFFERENT MELC LINES

| DS-1 g | 1st Day | 2nd Day | 5th Day Cell Count | 5th B+ | (5 day commitment) |
|---|---|---|---|---|---|
| Control | 0.38 | 1.1 | 2.8 | 0-1 | 0-1 |
| 5 mM HMBA | 0.2 | 0.5 | 2.0 | 91-90 | 88-88 |
| 0.5 mM IC-135 | 0.38 | 1 | 2.1 | 41-49 | 31-28 |
| 1 mM IC-135 | 0.33 | 0.8 | 1.4 | 72-74 | 51-58 |
| 2 mM IC-135 | 0.2 | 0.5 | 1.3 | 80-80 | 78-76 |
| 3 mM IC-135 | 0.2 | 0.5 | 1.2 | 87-88 | 81-80 |

| V3-17 | 1st Day | 2nd Day | 5th Day | 5th B+ | (5 day commitment) |
|---|---|---|---|---|---|
| Control | 0.4 | 1.2 | 2.9 | 3-6 | 0-1 |
| 5 mM HMBA | 0.23 | 0.5 | 1.6 | 98-99 | 99-98 |
| 0.5 mM IC-135 | 0.4 | 0.6 | 2.7 | 40-49 | 36-34 |
| 1 mM IC-135 | 0.31 | 0.44 | 1.3 | 89-83 | 89-91 |
| 2 mM IC-135 | 0.21 | 0.4 | 1.0 | 96-91 | 92-94 |
| 3 mM IC-135 | 0.23 | 0.3 | 0.9 | 98-97 | 99-99 |

| DR-10 | 1st Day | 2nd Day | 5th Day | 5th B+ | (5th day commitment) |
|---|---|---|---|---|---|
| Control | 0.41 | 1.0 | 2.9 | 0-1 | 0-0 |
| 5 mM HMBA | 0.3 | 0.48 | 2.1 | 90-89 | 1-4 |
| 0.5 mM IC-135 | 0.4 | 0.62 | 1.9 | 44-39 | 0-0 |
| 1 mM IC-135 | 0.32 | 0.48 | 1.4 | 70-74 | 0-1 |
| 2 mM IC-135 | 0.2 | 0.41 | 1.2 | 79-81 | 0-2 |
| 3 mM IC-135 | 0.2 | 0.40 | 1.2 | 88-86 | 1-3 |

REFERENCES

1. Breitman, T. R., Selonick, S. E., and Collins, S. J. Induction of differentiation of the human promyelocytic leukemia cell line (HL-60) by retinoic acid. Proc. Natl. Acad. Sci. USA., 77:2936–2940, 1980.

2. Olsson, I. L., and Breitman, T. R. Induction of differentiation of the human histiocytic lymphoma cell line U-937 by retinoic acid and cyclic adenosine 3':5'-monophosphate-inducing agents. Cancer Res., 42:3924–3927, 1982.

3. Schwartz, E. L., and Sartorelli, A. C. Structure-activity relationships for the induction of differentiation of HL-60 human acute promyelocytic leukemia cells by anthracyclines. Cancer Res., 42:2651–2655, 1982.

4. Marks, P. A., and Rifkind, R. A. Erythroleukemic differentiation. Annu. Rev. Biochem., 47:419–448, 1978.

5. Friend, C., Scher, W., Holland, J., and Sato, T. Hemoglobin synthesis in murine erythroleukemia cells in vitro: stimulation of erythroid differentiation by dimethylsulfoxide. Proc. Natl. Acad. Sci. USA, 68:378–382, 1971.

6. Marks, P. A., Sheffery, M., and Rifkind, R. A. Induction of transformed cells to terminal differentiation and the modulation of gene expression. Cancer Res. 47:659–666, 1987.

7. Fibach, E., Reuben, R. C., Rifkind, R. A., and Marks, P. A. Effect of hexamethylene bisacetamide on the commitment to differentiation of murine erythroleukemia cells. Cancer Res., 37:440–444, 1977.

8. Reuben, R. C., Khanna, P. L., Gazitt, Y., Breslow, R., Rifkind, R. A., and Marks, P. A. Inducers of erythroleukemic differentiation. Relationship of structure to activity among planar-polar compounds. J. Biol. Chem., 253:4124–4128, 1978.

9. Marks, P. A. and Rifkind, R. A. Hexamethylene Biscetamide Induced Differentiation of Transformed Cells: Molecular and Cellular Effects and Therapeutic Application. International Journal of Cell Cloning, 6:230–240, 1988.

10. Sporn, M. B., Roberts, A. B., Driscoll, J. S.: Principles of Cancer Biology: Growth Factor and Differentiation. In: Cancer Principles and Practic of Oncology Vol. 1: 2nd Edition. Eds. V. de Vita, S. Hellman and S. Rosenberg. Publ.: J. B. Lippincott Company, pgs. 49–65, 1985.

What is claimed is:

1. A method of treating a patient having a tumor characterized by proliferation of neoplastic cells which comprises administering to the patient an amount of a compound effective to selectively induce terminal differentiation of such neoplastic cells and thereby inhibit their proliferation, the compound having the structure:

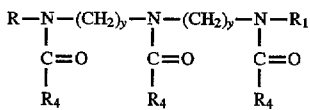

wherein each of R, $R_1$, and $R_4$ is a hydrogen atom or a methyl, ethyl or propyl group, R and $R_1$ are the same and R and $R_4$ are the same or different; and wherein y is 4, 5, 6 or 7.

2. A method of claim 1, wherein the compound has the structure:

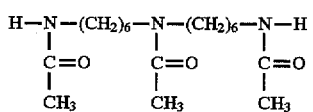

3. A method of claim 1, wherein the administering is effected once continuously for at least 5 days.

4. A method of claim 3, wherein the administering is effected once continuously for at least 10 days.

5. A method of claim 1, wherein the administering is effected at intervals of 5–35 days and continuously for at least 5 days each such interval.

6. A method of claim 1, wherein the amount of the compound is less than an amount which causes toxicity in the patient.

7. A method of claim 6, wherein the amount of the compound is from about 1 gm/m$^2$/day to about 30 gm/m$^2$/day.

8. A method of claim 1, wherein the tumor is a lung cancer, acute lymphold myeloma, bladder melanoma, renal carcinoma, breast carcinoma or colorectal carcinoma.

9. A method of claim 1, wherein the administering is effected intravenously.

10. A method of claim 1, wherein the administering is effected orally.

* * * * *